United States Patent
Anderson et al.

(10) Patent No.: US 9,272,137 B2
(45) Date of Patent: Mar. 1, 2016

(54) TRANSDERMAL METHODS AND SYSTEMS FOR THE DELIVERY OF ANTI-MIGRAINE COMPOUNDS

(75) Inventors: Carter R. Anderson, Inver Grove Heights, MN (US); Russell L. Morris, Lindstrom, MN (US); Terri B. Sebree, Gladwyne, PA (US)

(73) Assignee: Teva Pharmaceuticals International GmbH, Rapperswil-Jona (CH)

( * ) Notice: Subject to any disclaimer, the term of this patent is extended or adjusted under 35 U.S.C. 154(b) by 148 days.

(21) Appl. No.: 13/105,562

(22) Filed: May 11, 2011

(65) Prior Publication Data

US 2011/0213294 A1 Sep. 1, 2011

Related U.S. Application Data

(60) Division of application No. 12/181,142, filed on Jul. 28, 2008, now Pat. No. 7,973,058, which is a continuation of application No. PCT/US2007/009000, filed on Apr. 12, 2007.

(60) Provisional application No. 60/791,819, filed on Apr. 13, 2006, provisional application No. 60/814,131, filed on Jun. 16, 2006.

(51) Int. Cl.
   *A61N 1/30* (2006.01)
(52) U.S. Cl.
   CPC ........................................ *A61N 1/30* (2013.01)
(58) Field of Classification Search
   USPC ......................................................... 514/323
   See application file for complete search history.

(56) References Cited

U.S. PATENT DOCUMENTS

| | | | |
|---|---|---|---|
| 4,557,723 A | 12/1985 | Sibalis | |
| 4,822,802 A | 4/1989 | Levy et al. | |
| 4,883,457 A | 11/1989 | Sibalis | |
| 4,927,408 A | 5/1990 | Haak et al. | |
| 5,042,975 A | 8/1991 | Chien et al. | |
| 5,162,042 A * | 11/1992 | Gyory et al. | 604/20 |
| 5,207,752 A | 5/1993 | Sorenson et al. | |
| 5,358,483 A | 10/1994 | Sibalis | |
| 5,458,569 A | 10/1995 | Kirk, III et al. | |
| 5,466,217 A | 11/1995 | Myers et al. | |
| 5,533,971 A | 7/1996 | Phipps | |
| 5,605,536 A | 2/1997 | Sibalis | |
| 5,651,768 A | 7/1997 | Sibalis | |
| 5,685,837 A | 11/1997 | Horstmann et al. | |
| 5,697,896 A | 12/1997 | McNichols et al. | |
| 5,807,571 A * | 9/1998 | List | 424/449 |
| 5,882,677 A | 3/1999 | Kupperblatt | |
| 5,941,843 A | 8/1999 | Atanasoska et al. | |
| 5,983,130 A | 11/1999 | Phipps et al. | |
| 6,035,234 A | 3/2000 | Riddle et al. | |
| 6,090,095 A | 7/2000 | McNichols et al. | |
| 6,171,294 B1 | 1/2001 | Southam et al. | |
| 6,216,033 B1 | 4/2001 | Southam et al. | |
| 6,245,347 B1 | 6/2001 | Zhang et al. | |
| 6,421,561 B1 | 7/2002 | Morris | |
| 6,425,892 B2 | 7/2002 | Southam et al. | |
| 6,653,014 B2 | 11/2003 | Anderson et al. | |
| 6,678,555 B2 | 1/2004 | Flower et al. | |
| 6,745,071 B1 * | 6/2004 | Anderson et al. | 604/20 |
| 6,842,640 B2 * | 1/2005 | Riddle et al. | 604/20 |
| 6,975,902 B2 | 12/2005 | Phipps et al. | |
| 7,018,370 B2 | 3/2006 | Southam et al. | |
| 7,302,293 B2 | 11/2007 | Southam et al. | |
| 7,937,141 B1 | 5/2011 | Inoue et al. | |
| 7,973,058 B2 | 7/2011 | Anderson et al. | |
| 8,470,853 B2 * | 6/2013 | Anderson et al. | 514/323 |
| 2003/0013753 A1 * | 1/2003 | Aung-Din | 514/419 |
| 2003/0124179 A1 | 7/2003 | Jacobsen et al. | |
| 2004/0242770 A1 | 12/2004 | Feldstein et al. | |
| 2005/0148996 A1 | 7/2005 | Sun et al. | |
| 2005/0228336 A1 | 10/2005 | Keusch et al. | |
| 2006/0253061 A1 | 11/2006 | Anderson et al. | |
| 2007/0093788 A1 | 4/2007 | Carter | |

FOREIGN PATENT DOCUMENTS

| | | |
|---|---|---|
| CA | 2160776 | 4/1994 |
| EP | 0904779 A2 | 3/1999 |
| JP | A S60-60860 | 12/1985 |
| JP | H8-238325 | 11/1989 |
| JP | A H8-509749 | 4/1994 |
| JP | H9-510387 | 9/1995 |
| JP | 2000000314 A | 1/2000 |
| JP | 2003530909 A | 10/2003 |
| JP | 2003310769 A | 11/2003 |
| WO | 91/15258 A1 | 10/1991 |
| WO | WO 95/25562 | 9/1995 |
| WO | 96/40365 A1 | 12/1996 |
| WO | 97/11743 A1 | 4/1997 |
| WO | 2005/120482 A1 | 12/2005 |

OTHER PUBLICATIONS

Font, A. F. et al., "Iontophoretic transdermanl delivery of sumatriptan: effect of current density and ionic strength", J. Pharm. Sci., vol. 94, 10., p. 2183-2186, Oct. 2005.

Van der Geest, R. et al., Non-invasive assessment of skin barrier integrity and skin irritation following iontophoretic current application in humans, J. Control. Release, vol. 41, No. 3, p. 205-213, Sep. 1996.

ALZA Corporation (JNJ) Receives FDA Approval for IONSYS™ (Fentanyl Iontophoretic Transdermal System), retrievied online at http://www.biospace.com/news_story.aspx?NewsEntityId=19447 &source=news-email (2006).

Anderson, Carter R. et al., "Effects of Iontophoresis Current Magnitude and Duration of Dexamethasone Deposition and Localized Drug Retention," *Physical Therapy*, vol. 83:161-170 (2003).

Anderson, Carter R. et al., "Quantification of Total Dexamethasone Phosphate Delivery by Iontophoresis," *International Journal of Pharmaceutical Compounding*, vol. 7(2):155-159 (2003).

(Continued)

*Primary Examiner* — Michael B Pallay
(74) *Attorney, Agent, or Firm* — McCarter & English, LLP; Danielle L. Herritt, Esq.

(57) ABSTRACT

Iontophoretic patches for the delivery of anti-migraine compounds and methods of using the patches are described.

15 Claims, 6 Drawing Sheets

(56) References Cited

OTHER PUBLICATIONS

Banga, Ajay K. et al., "Iontophoretic Delivery of Drugs: Fundamentals, Developments and Biomedical Applications," *Journal of Controlled Release*, vol. 7:1-24 (1988).

Chaturvedula, Ayyappa et al., "Dermal, Subdermal, and Systemic Concentrations of Granisetron by Iontophoretic Delivery," *Pharmaceutical Research*, vol. 22(8):1313-1319 (2005).

Chaturvedula, Ayyappa et al., "In vivo iontophoretic delivery and pharmacokinetics of salmon calcitonin," *International Journal of Pharmaceutics*, vol. 297:190-196 (2005).

Christensen, Michael L. et al., "Pharmacokinetics of Sumatriptan Nasal Spray in Adolescents," *J. Clin. Pharmacol.*, vol. 43:721-726 (2003).

Duquesnoy, C. et al., "Comparative clinical pharmacokinetics of single doses of sumatriptan following subcutaneous, oral, rectal and intranasal administration," *European Journal of Pharmaceutical Sciences*, vol. 6:99-104 (1998).

Femenia-Font, A. et al. "Effect of chemical enhancers on the in vitro percutaneous absorption of sumatriptan succinate," *European Journal of Pharmaceutics and Biopharmaceutics*, 61:50-55 (2005).

Femenia-Font, A. et al., "Iontophoretic Transdermal Delivery of Sumatriptan: Effect of Current Density and Ionic Strength," *Journal of Pharmaceutical Sciences*, vol. 94(10):2183-2186 (2005).

Fouchard, D. et al. "Effects of iontophoretic current flow on hairless rat skin in vivo," *Journal of Controlled Release*, 49:89-94 (1997).

Jadoul, Anne et al., "Transdermal Permeation of Alniditan by Iontophoresis: In Vitro Optimization and Human Pharmacokinetic Data," *Pharmaceutical Research*, vol. 13(9):1348-1353 (1996).

Jhee, Stanford S. et al., "Pharmacokinetics and Pharmacodynamics of the Triptan Antimigraine Agents," *Clin. Pharmacokinet.*, vol. 40(3):189-205 (2001).

Kalia, Y. et al., "Transdermal iontophoretic delivery of antimigraine therapeutics in vivo," *2004 AAPS Annual Meeting and Exposition*, (2004).

Lattin, Gary A. et al., "Electronic Control of Iontophoretic Drug Delivery," *Annals of the New Yorker Academy of Sciences*, vol. 618:450-464 (1991).

Patel, Sonal R. et al., "In vitro and in vivo evaluation of the transdermal iontophoretic delivery of sumatriptan succinate," *European Journal of Pharmaceutics and Biopharmaceutics*, vol. 66:296-301 (2007).

Patel, Sonal R. et al., "Transdermal iontophoresis of sumatriptan succinate in vitro," *205th Meeting, The Electrochemical Society, Inc.*, Abs. 725 (2004).

Patel, S.R. et al., "Transdermal iontophoretic delivery of sumatriptan in vitro," Cephalalgia, Abstracts of the 15th Migraine Trust International Symposium, (2004).

Pierce, M. et al., "NP101: A novel Formulation of Sumatriptan Succinate Utilizing SmartRelief™ Transdermal Technology," *50th Annual Scientific Meeting, American Headache Society*, p. S46, No. S17 (2008).

Scholpp, J. et al., "Early treatment of a migraine attack while pain is still mild increases the efficacy of sumatriptan," *Cephalalgia*, vol. 24:925-933 (2004).

Siegel, Steven J. et al., "A Unique Iontophoretic Patch for Optimal Transdermal Delivery of Sumatriptan," *Pharmaceutical Research*, vol. 24(10):1919-1926 (2007).

Vyteris Announces Positive Results for Phase I Clinical Trial, *Vyteris Holdings (Nevada), Inc.* (2005).

Vyteris, "The smart patch by vyteris, The future of drug delivery . . . today!" JP Morgan 25th Annual Healthcare Conference (Jan. 2007).

Xu, Xiaohui et al., "Determination of degradation products of sumatriptan succinate using LC-MS and LC-MS-MS," *Journal of Pharmaceutical and Biomedical Analysis*, vol. 26:367-377 (2001).

International Search Report and Written Opinion for No. PCT/US07/09000.

Office Action issued by the Canadian Intellectual Property Office for Application No. 2,650,412 mailed Nov. 26, 2013 (3 pages).

Notice of Reasons for Rejection and English translation issued by the Japanese Patent Office for Application No. 2014-141927 mailed Jun. 8, 2015.

Extended European Search Report for EP Application No. 07755312.1 dated Jun. 22, 2015 (6 pages).

Office Action issued by the India Intellectual Property Office for Application No. 6176/CHENP/2008 mailed Jun. 12, 2015 (2 pages).

Further Examination Report issued by the New Zealand Intellectual Property Office for Application No. 610790 mailed Dec. 1, 2014 (3 pages).

\* cited by examiner

TRANSDERMAL METHODS AND SYSTEMS FOR THE DELIVERY OF ANTI-MIGRAINE COMPOUNDS

RELATED APPLICATIONS

This application is a divisional application of U.S. application Ser. No. 12/181142, filed Jul. 28, 2008, which, in turn, is a continuation of PCT application number PCT/US2007/009000 filed on Apr. 12, 2007, which claims priority based on U.S.Provisional Patent Application Ser. No. 60/791,819, filed on Apr. 13, 2006, and U.S. Provisional Patent Application Ser. No. 60/814,131, filed on Jun. 16, 2006. Each of these applications is incorporated herein by reference in their entirety.

BACKGROUND OF THE INVENTION

I. Field of the Invention

The present invention is related generally to transdermal delivery of active anti-migraine compounds by the use of an applied electro motive force (emf), commonly known as iontophoresis. Specifically, this invention relates to an improved device for the delivery of anti-migraine drugs, particularly triptan serotonin agonists including Sumatriptan and Naratriptan. Further, this invention provides a wearable iontophoresis system, which can be used to provide both rapid pain relief and sustained action for the prevention of pain recurrence.

II. Related Art

The process of iontophoresis was described by LeDuc in 1908 and has since found commercial use in the delivery of ionically charged therapeutic agent molecules such as pilocarpine, lidocaine and dexamethasone. In this delivery method, ions bearing a positive charge are driven across the skin at the site of an electrolytic electrical system anode while ions bearing a negative charge are driven across the skin at the site of an electrolytic system cathode.

Earlier, and some present, iontophoretic devices have been typically constructed of two electrodes attached by adhesive materials to a patient, each connected by a wire to a remote power supply, generally a microprocessor-controlled electrical instrument.

More recently, self-contained wearable iontophoretic systems have been developed. These systems are advantageous in that they do hot have external wires and are much smaller in size. Examples of such systems can be found in a variety of U.S. patents, including U.S. Pat. Nos. 4,927,408; 5,358,483; 5,458,569; 5,466,217; 5,533,971; 5,605,536; 5,651,768; 5,685,837; 6,421,561; 6,425,892; 6,653,014; and 6,745,071. These systems are also comprised of two electrodes fixed to patients by means of adhesive materials.

Migraine is a condition that affects approximately 10% of the adult population worldwide, yielding approximately 600 million people with about 28 million in the US alone. (L. Morillo. Migraine headache. Am Fam Physician. 65:1871-1873 (2002); L. E. Morillo. Migraine headache. Clin Evid: 1547-1565 (2003); and L. E. Morillo. Migraine headache. Clin Evid:1696-1719 (2004)) Females suffer from migraine headache three fold more frequently than males. (E. Lawrence. Diagnosis and Management of Migraine Headaches. Southern Medical Journal. 97:1069-1077 (2004)) Migraine headache is associated with inflamed and dilated blood vessels leading to severe unilateral pain that worsens with physical activity. (The International Classification of Headache Disorders. Cephalagia. 24, Supplement 1: (2004)) In addition to headache pain, migraine can be associated with a variety of other symptoms, including diarrhea, cold extremities, facial pallor, nausea, vomiting and sensitivity to external stimuli such as light, sounds or odors. Approximately one fifth of migraine patients experience an aura or visual symptoms, such as spots of light, zigzag lines, or a graying out of vision. (Cephalagia (2004) and J. Scholpp, R. Shellenberg, B. Moeckesch, and N. Banik. Early treatment of a migraine attack while pain is still mild increases the efficacy of Sumatriptan. Cephalagia. 24:925-933 -(2004))

Migraines typically last for up to 24 hours, but can range from 4 to 72 hours and patients often experience migraine attacks one to two times per month. Migraines can be triggered by many different factors, including life stressors, certain foods or dietary habits, shifts in circadian rhythms, schedules or sleep patterns and changes in weather such as barometric pressure or altitude as well as cyclic variation in hormonal levels during the menstrual cycle. (Cephalagia (2004) and F. D. Sheftell, R. E. Weeks, A. M. Rapoport, S. Siegel, S. Baskin, and F. Arrowsmith. Subcutaneous Sumatriptan in a clinical setting: the first 100 consecutive patients with acute migraine in a tertiary care center. Headache. 34:67-72 (1994))

Pharmacologic interventions constitute the mainstay of treatment for migraines and are available for both acute treatment (abortive) and prevention (prophylactic). Mild migraine can often be effectively treated with over-the-counter medications including aspirin, acetaminophen, NSAIDs, and combination products that include caffeine.

Triptans are the mainstay of treatment for acute migraine of moderate to severe intensity. (E. Lawrence (2004)) When these agents are used early in the course of an attack, triptans abort more than 80% of migraines within two hours. (J. Scholpp et al. (2004)) However, several different triptan products are available with variation in the efficacy and tolerability of different medications in this class. Triptans are also available in a variety of formulations (oral, dissolvable tablet, nasal spray and injectable). Non-oral formulations are typically used for patients with gastrointestinal symptoms of nausea or vomiting and/or when a more rapid onset of action is desired.

Triptans are thought to work by activating serotonin (5-HT) receptors on trigeminovascular nerve endings, inhibiting the release of neurotransmitters that cause painful cranial vasodilatation. (C. M. Sumatriptan.) Furthermore, triptans produce active vasoconstriction and may relieve symptoms of migraine by stimulating 5-HT receptors on cranial vessels. Sumatriptan is the most widely prescribed triptan, comprising roughly half of all triptan prescriptions between 2002 and 2004.

Currently marketed Sumatriptan formulations each have advantages and disadvantages. The injection and intranasal formulations offer rapid onset of action and may reduce further gastrointestinal discomfort. The injection also provides a good response in most patients, but yields a higher maximum concentration that may contribute to a higher side effect burden. However, many patients do not like the discomfort and inconvenience of the injection and the bitter taste of the intranasal formulation. The oral formulation offers convenience and ease of use but produces unreliable blood levels and inconsistent response. Recurrence (rebound) occurs with all three Sumatriptan formulations.(P. Tfelt-Hansen. Efficacy and adverse events of subcutaneous, oral, and intranasal Sumatriptan used for migraine treatment: a systemic review based on number needed to treat. Cephalagia. 18:532-538 (1998).) This common problem with recurrence is likely due to persistence of the original event with a time course exceeding the duration of action from the currently available formulations. This is particularly so because Sumatriptan has a serum elimination half-life of only 2 hrs and most of the active drug is eliminated within 4-6 hrs. in the majority of patients.

A recent publication has indicated that Sumatriptan can be transdermally transported effectively using iontophoresis (Femenia-font et al, J. Pharm Sci 94, 2183-2186, 2005). In this study, iontophoretic transport of Sumatriptan was found to be at a rate 385 fold higher than passive transport. U.S. Pat. No. 5,807,571 contemplates both iontophoretic and passive transdermal delivery of Sumatriptan and other serotonin agonists.

Another recent study has concluded that iontophoresis can be useful in the delivery of anti-migraine compounds (reference Vyteris press release, Sep. 20, 2005). In this study, a two-component system comprised of an electronic controller connected by wire to a transdermal patch was used to deliver Zolmatriptan. The company presenting the results from this study has concluded that programmable capability of its iontophoresis units may allow rapid initial delivery for fast action, while a sustained, low level maintenance dose can be utilized for a prevention of headache recurrence. A significant limitation of this device lies in the two-component structure of the delivery system; the wire connections between the controller and patches are a nuisance to the wearer. Additionally, programmable controllers can be expensive if utilized on a single use basis, or lost, contaminated, broken, etc. if utilized on a reusable basis.

Others have speculated that two-step delivery profiles can be useful an iontophoretic device with rapid onset and sustained action. For example, U.S. Pat. No. 5,207,752 describes a two-stage iontophoretic delivery process that can be utilized to create a drug delivery profile with a first stage in order to rapidly to reach therapeutic level, and an appropriately timed second stage at a lower delivery rate to maintain the blood levels at the therapeutic level. While theoretically sound, this technique will be difficult to use in practice, because the attainment and maintenance of the therapeutic level will have unique timing requirements for each individual patient. Body sizes, drug metabolism, therapeutic blood level, etc. are critical individual factors which will influence the precise timing necessary to switch from high delivery rates to lower ones.

The '752 patent also describes a means to further enhance the rate of therapeutic response, using a three step process. In this embodiment, a first high level of current is applied so the blood levels will exceed the average required therapeutic blood level, the current is ceased for a time period for the blood levels to reach a minimum necessary blood level, then a low level current is at a third time point in order to maintain a lower therapeutic blood level. While this process can provide an advantage in onset of action, the three-step process will require complex current control mechanisms. Given the low cost requirements for simple, disposable wearable devices, a complex three-step process may render the device cost prohibitive on a practical basis for commercial sale.

Others have disclosed simple, low-cost devices structured for waveform delivery patterns with iontophoresis. U.S. Pat. No. 6,421,561, assigned to the same assignee as the present invention, describes very simple electrical circuits that can be used to create low-cost, disposable patches providing multiple current levels in an automated fashion. That reference describes circuits suitable for use with the present invention.

Thus, given the above, there exists the need for an optimal product that would seek to provide the advantages of rapid, systemic Sumatriptan administration found in an injection without the need for an injection and with a consistent duration of action which exceeds the effective time of an injection course of the patient's migraine.

SUMMARY OF THE INVENTION

The present invention provides an iontophoretic device that is wearable and a method for operating the device. Both the device and the method are specifically designed for the delivery of active serotonin agonists in the form of triptan compounds including, for example, Sumatriptan, Naratriptan and others, such as those shown in Table I, or salts thereof such as succinates, hydrochlorides, etc. recognized as useful in the treatment of triptan compound responsive states, such as migraine headaches.

The invention also provides multi-dosage rate devices that can provide waveform optimized dosage delivery patterns that can be used to provide minimal time for onset of action, while providing maximum time for therapeutic benefit thereafter. The present invention provides this result using, for example, a simplified two-stage delivery pattern to create an initial peak dosage level, supplying an effective amount of anti-migraine agent in less than one hour, before falling to a lower sustained therapeutic level in a subject's blood.

Another important aspect of the present invention relates to skin irritation. It is well known that current densities should be kept low in order to minimize skin irritation from current flow. By means of the present invention, desired optimized dosage patterns are realized while maintaining safe current density levels thereby minimizing skin irritation effects. In this regard, it has been discovered that safe levels of current density vary and are actually lower than those suggested in the literature. Safe levels likely depend on effects that are specific to the drug utilized, wearing conditions, and the specific dosage pattern. Accordingly, it has been found that preferred current densities determined for the agents transported in the present invention are generally between 25 and 200 microamps per square centimeter, but may be as high as about 250 microamps per square centimeter in certain cases. While a safe level is considered to be one in which the mean skin erythema score is 2.5 or less immediately after patch removal, a value of 2.0 or less is preferred and a value of 1.0 or less is most preferred.

The present invention also provides the formulated content of triptans in the iontophoretic delivery chambers required to maintain efficient delivery for the delivery period. It has been found, for example, that the amount of Sumatriptan contained in the patch must be at least three fold higher than the desired delivery dosage in order to provide a uniform delivery rate. A preferred formulation in accordance with the invention may also incorporate a hydrogel material. The hydrogel serves to retain the drug formulation in the reservoir, unlike free flowing liquids which are more prone to leakage during body movement. Further, the hydrogel is best provided as a very viscous fluid, which enables an optimal skin contact and minimizes skin irritation. An example of a preferred viscous fluid is a 2% hydroxypropylmethylcellulose (HPMC) or polyvinylpyrrolidinone (PVP).

Effective levels of the active agent in a subject's blood will vary with the agent used, severity of condition, etc. For this reason, a variety of patch dosages can be made available both as to amount and duration of sustained application.

Several embodiments have been developed. In a first embodiment of this invention, a device and delivery pattern is provided which has been discovered to be an optimal delivery rate for Sumatriptan in order to provide a two-stage iontophoretic transdermal device for similar or superior efficacy to 50 mg oral delivery dosing forms. In a second embodiment, a two-stage device and delivery pattern is described to provide a dosage similar or superior to efficacy of 20 mg nasal delivery forms for Sumatriptan. In a third embodiment, two-stage patterns are described for the delivery of Naratriptan for similar or superior efficacy to 2.5 mg oral dosage forms.

Although some embodiments utilize a two-stage delivery pattern to create an initial peak dosage level followed by a period of a lower sustained therapeutic level in a subject's blood, anti-migraine agents can also be administered to a subject utilizing a single stage. If this approach is used, however, the quick initial peak dosage level of administration may be replaced by a somewhat delayed sustained therapeutic level which may be advisable in some cases.

One aspect of the invention pertains to methods for delivering therapeutic anti-migraine agents using an iontophoretic transdermal patch. One method includes (a) providing an iontophoretic transdermal patch containing an amount of an active anti-migraine agent in the form of a triptan compound, to be administered; (b) using a two-stage patterned delivery sequence, preferably uninterrupted and which may include an initial first stage delivery at a relatively high rate followed by a second stage delivery at a lower rate to provide a waveform delivery pattern in which a therapeutically effective dosage level is reached in a subject in generally less than one hour and a maintenance level is continued for one or more hours.

The invention pertains, at least in part, to an iontophoretic transdermal patch for the delivery of anti-migraine agents dedicated to a two-stage administration sequence in which an initial or first stage delivery rate exceeds a second stage delivery rate to produce a waveform delivery pattern. In a further embodiment, the patch may be characterized by a power/area ratio such that the average current density is less than 250 $\mu A/cm^2$.

The invention also includes an integrated iontophoretic transdermal patch for the delivery of a triptan compound or a salt thereof. The patch allows for the delivery of an effective amount of a triptan compound to a subject in less than one hour. The patch is capable of maintaining a steady state concentration of the triptan compound in the subject at a desired concentration for at least one hour. The patch also uses a current density selected such that the current does not substantially irritate the skin of a subject without damaged or denuded skin.

One embodiment involves an iontophoretic transdermal patch for the delivery of a Sumatriptan or a salt thereof which patch allows for the systemic delivery of an effective amount of Sumatriptan or a salt thereof to a subject.

The patch may use a multi-stage patterned delivery.

One two-stage patterned delivery includes a first stage which averages approximately 3 mA for about 30 minutes, followed by a second stage which averages approximately 1.5 mA for at least 1 or more hours. Another two-stage patterned delivery includes a first stage which averages approximately 1 mA for about 45 minutes, followed by a second stage which averages approximately 0.5 mA for about 1 or more hours.

Another embodiment involves an iontophoretic transdermal patch for the delivery of naratriptan or a salt thereof using a two-stage patterned delivery, wherein the two-stage patterned delivery comprises a first stage which averages approximately 1 mA for at least a significant portion of 45 minutes, followed by a second stage which averages approximately 0.25 mA for at least one hour.

The invention also pertains to a method for treating a subject, by transdermally administering to a subject an effective amount of a triptan compound in less than one hour using an integrated iontophoretic patch, wherein the patch uses a current density selected such that the current does not substantially irritate the subject's skin.

The invention also involves a method for treating a subject for a triptan compound responsive state by administering transdermally to a subject a steady state concentration of a triptan compound for at least one hour. The method for treating a triptan compound responsive state in a subject may enable administering to a subject an effective steady state concentration of a triptan compound transdermally using a fully integrated patch.

BRIEF DESCRIPTION OF THE DRAWINGS

In the Figures:

In FIG. 2A, Data are displayed on a linear scale.

DETAILED DESCRIPTION

Figure 1:
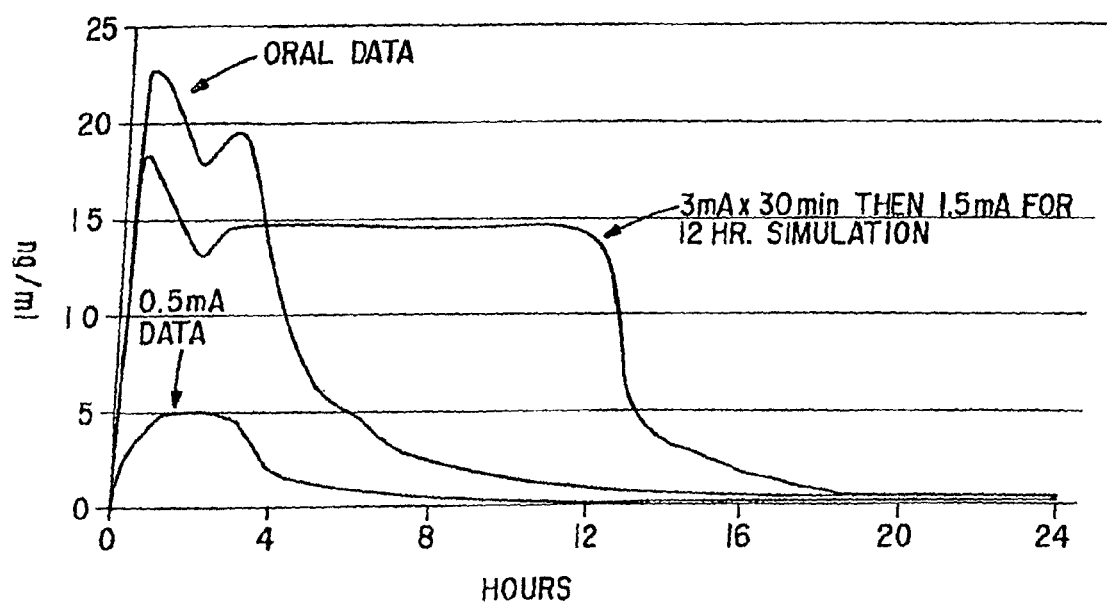
FIG. 1 is a graphical representation of blood concentration levels measured based on Sumatriptan dosing by three methods, namely, 50 milligram oral tablet, iontophoretic dosing after application of a 0.5 mA of total current for three hours, and a simulation of a delivery pattern in accordance with the invention.
Figure 2A:
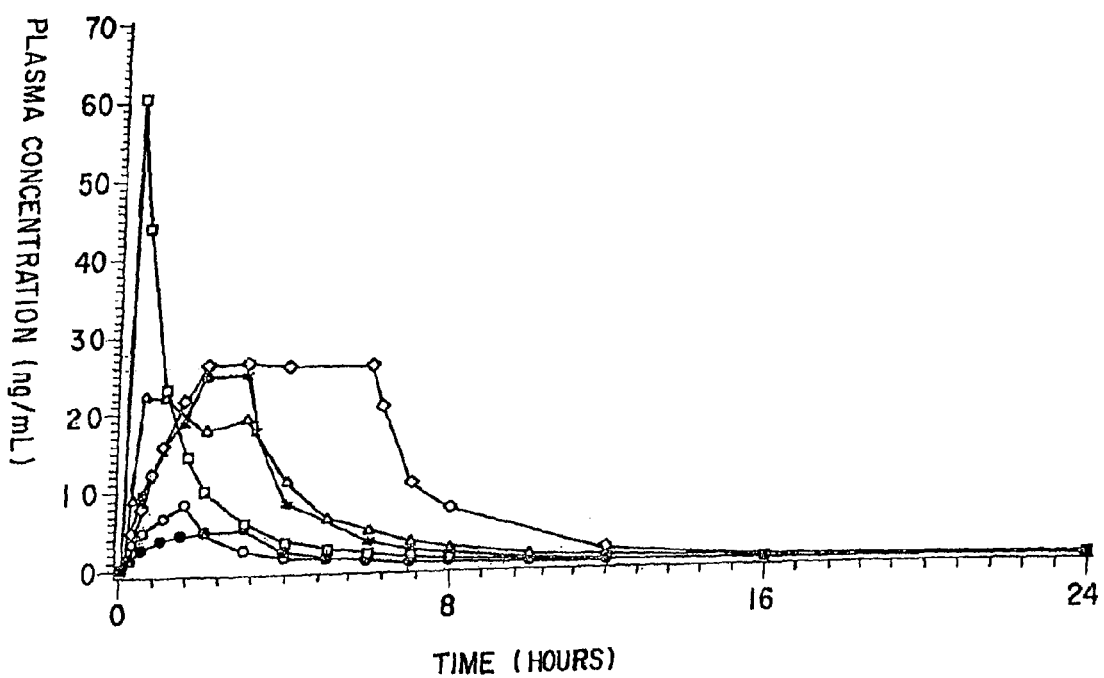
FIG. 2A illustrates Mean Sumatriptan Plasma Concentration Profiles.
Figure 2B:
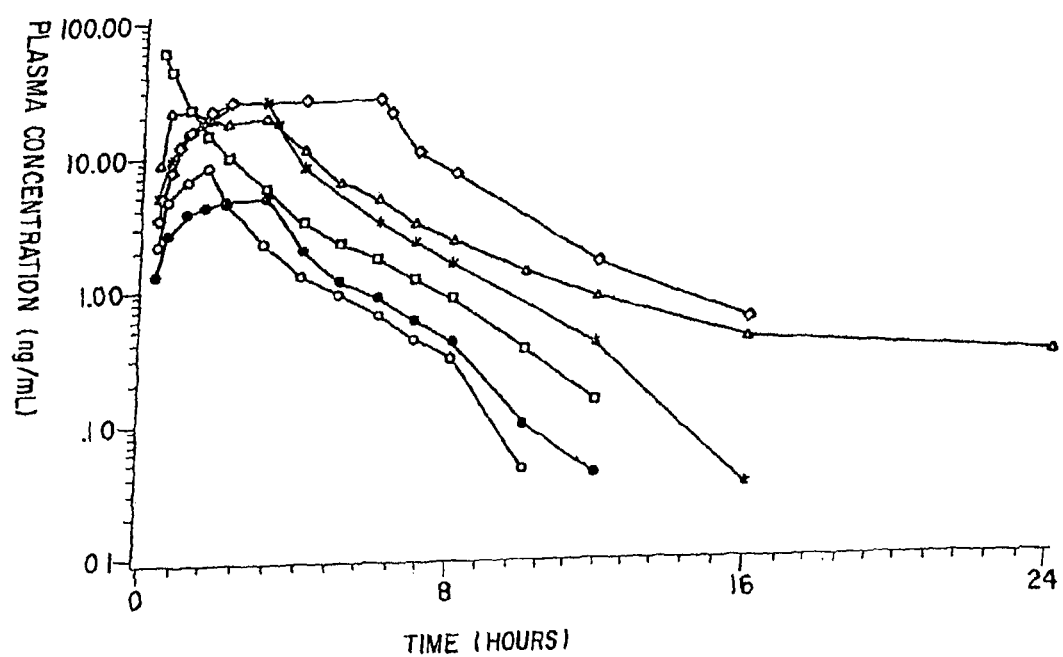
FIG. 2B shows the Data displayed using a Semi-Log scale. The tick marks on the x-axis represent 10ths of each 8 hour interval or approximately 48 minutes each. Symbols: Triangles—Treatment 1 (Sumatriptan 50 mg oral tablet); Squares—Treatment 2 (Sumatriptan 6 mg subcutaneous injection); Open circles—Treatment 3 (1.0 mA patch, 1.5 hr); Closed circles—Treatment 4 (0.5 mA patch, 3.0 hr); Stars—Treatment 5 (two 1.0 mA patches, 3.0 hr); Diamonds—Treatment 6 (two 1.0 mA patches, 6.0 hr)

The following description includes detailed information regarding certain embodiments of the present invention. These are presented as examples of inventive concepts rather than as limitations on them. Other embodiments, variations and combinations as will occur to those skilled in the art are also contemplated to be within the scope of the invention.

1. Definitions

In addition to any terms defined elsewhere used in the present application, the following definitions apply.

The term "iontophoretic transdermal patch" includes integrated devices which allow for the administration of therapeutic compounds through the skin by using electrical current to promote the absorption of the compound from the patch through the skin of the subject. In particular, in the therapeutic compounds of the present invention are triptan compounds in any form suitable for transdermal administration using iontophoresis.

The term "integrated" means completely self-contained and means patches which contain the drug, power source, and all other necessary components to deliver the drug ionotophoretically in a single wearable patch. The term "integrated", thus, denotes patches which do not require a separate power source or controller.

The term "shelf life" includes the period of time that the complete patch can rest unused in ambient temperature and moisture levels and still be used to perform its intended function, e.g., administer the desired compounds to treat a subject.

The term "triptan compound" means triptan compounds, derivatives and salts of triptan compounds. The term also includes compounds that contain a 2-(1H-indol-3-yl)-N,N-dimethylethanamine moiety. Examples of triptan compounds some of which are listed in Table I include, but are not limited to, almotriptan, frovatriptan, eletriptan, zolmitriptan, rizatriptan, Sumatriptan, naratriptan, and pharmaceutically acceptable salts thereof.

The term "subject" includes living organisms capable of having triptan compound responsive states (e.g., mammals). Examples of subjects include humans, dogs, cats, horses, cows, sheep, goats, rats and mice. The term is meant to include subjects suffering from a triptan compound responsive state.

The term "effective amount" means the amount of the triptan compound which is effective to treat a particular triptan compound responsive state.

The term "treat" means the reduction or amelioration of one or more symptoms of a triptan compound responsive state. It also may mean the prevention of the occurrence or reoccurrence of a triptan compound responsive state.

The term "triptan compound responsive states" means almotriptan responsive states, zolmitriptan responsive states, rizatriptan responsive states, Sumatriptan responsive states, and naratriptan responsive states. The term also includes migraines, familiar hemiplegic migraines (with and without aura), chronic paroxysmal headaches, cluster headaches, migraine headaches, basilar migraines, and atypical headaches accompanied by autonomic symptoms. Typically, the triptan compound responsive state is a migraine.

The term "delivery" means the transport of the triptan compound from the patch to the blood, plasma, or cerebrospinal fluid of a subject.

The term "systemic delivery" means delivery to a subject through non-oral administration. Preferred systemic administration methods include transdermal administration.

The term "delivery time" is defined as the period of time which the patch is functioning by actively delivering the triptan compound to the subject iontophoretically.

The term "maintain a steady state concentration" refers to the maintenance of a particular concentration (e.g., a desired concentration, e.g., an effective amount) for a particular length of time.

The term "significant portion" may vary with context. It may mean at least 30% of the delivery time or more, at least 40% of the delivery time or more, at least 50% of the delivery time or more, at least 60% of the delivery time or more, at least 70% of the delivery time or more, at least 75% of the delivery time or more, at least 80% of the delivery time or more, at least 85% of the delivery time or more, at least 90% of the delivery time or more, or at least 95% of the delivery time or more.

The term "does not substantially irritate a subject's skin" means patches which result in a skin erythema score of 2.50 or less, 2.00 or less, or 1.00 or less about two hours after patch removal. In some embodiments, the language "does not substantially irritate a subject's skin" includes patches which result in a skin erythema score of 2.50 or less, 2.00 or less, or 1.00 or less immediately after patch removal.

The term "transdermal" includes delivery methods which occur through the skin of a subject without puncturing the subject's skin.

2. Iontophoretic Patches of the Invention

One aspect of the invention pertains to an integrated iontophoretic transdermal patch for the delivery of a triptan compound or a salt thereof. In one embodiment, an integrated patch comprises electrical components, the triptan compound, and an adhesive backing layer.

The concentrations of the triptan compound in the blood to maintain an effective amount will vary with the compound used. As shown in FIG. 1, in the case of Sumatriptan, an initial dose of 10-20 ng/mL may generally be effective. However, an initial concentration between 15 and 20, possibly 22.5 ng/mL, may be desired.

Table I shows additional triptan pharmacokinetics where $c_{max}$ is the expected maximum concentration in the patient's blood and AUC is the total dosage.

TABLE I

Triptan Pharmacokinetics

| Drug | $C_{max}$ ng/mL | AUC ng · hr/mL |
|---|---|---|
| Almotriptan | 52 | 310 |
| Frovatriptan | 5 | 45 |
| Eletriptan | 200 | 1,300 |
| Naratriptan | 8 | 75 |
| Rizatriptan | 22 | 78 |
| Zolmitriptan | 4 | 20 |

Examples of pharmaceutically acceptable salts of triptan compounds which may be used in the methods and patches of the invention include, but are not limited to, chloride, bromide, iodide, sulfate, phosphate, lactate, citrate, tartarate, salicylate, succinate, maleate, gluconate, mesylate, laurate, dodecylate, myristate, palmitate, stearate, coconoate, behinate, oleate, linoleate, linolenate, eicosapentaenoate, eicosahexaenoate, docosapentaenoate, docosahexaenoate, eicosanoids and the like. One triptan compound successfully used is Sumatriptan succinate. In certain embodiments, the salt of the triptan compound may be selected such that it does not react with the other components of the patch, such as the metal electrode. In certain embodiments, the salt may be advantageously selected such that it does not form a significant amount of an insoluble residue when in contact with the metal components of the patch of the invention.

One advantage of the iontophoretic patch of the present invention is that it is integrated and is wearable and lightweight. One example of an integrated iontophoretic patch is shown in the exploded view of FIG. 3A and assembled view with parts exposed of FIG. 3B. The device, generally at 10, includes a bottom overlayer of a release liner 12. Saline and drug reservoirs are indicated at 24 and 22, respectively. A double retaining ring overlayer 18 is provided which may be of a foam material. The power source with all electrical components is shown in layer 20 is shown in greater detail in the circuit diagram depicted in FIG. 4. Finally, an outer or overlay protective layer is shown at 26. FIG. 4 depicts a schematic circuit diagram suitable for use in the patch embodiment of FIGS. 3A and 3B or other patches in accordance with the present invention. The diagram is shown generally at 40 and includes a voltage source 42 which include a plurality of serially connected (possible 3 to 5) 3-volt lithium button cells which may be Panasonic CR2016 or similar cells. A pair of spaced, isolated anodes, preferably containing zinc are shown at 44 and 46. The anodes may be of unequal capacity. For example anode 44 may have a capacity of 90 mA min and anode 46 may have a capacity of 540 mA min. The circuit also includes a cathode 48, or indifferent electrode, which may be silver chloride, a pair of control transistors are shown at 50 and 52 in conjunction with parallel resistors 54 and 56, respectively. The transistors may be Fairchild semiconductor MMBF 5457 or equivalent, for example. The resistors 54 and 56 are sized to trim the current to a desired value such as 1.5 mA. Each of the anodes may be connected to the circuit by an exposed silver "wearbar", as indicated at 58 and 60, each of which consists of a thin layer of a consumable conductive strip, normally silver, which, when severed by consumption cuts off and isolates an associated connected anode. Such devices and techniques are illustrated and described in U.S. Pat. No. 7,013,769 assigned to the same assignee as the present invention and incorporated herein in its entirety for any purpose. These provide positive disconnects according the predesigned capacities.

Figure 3A:
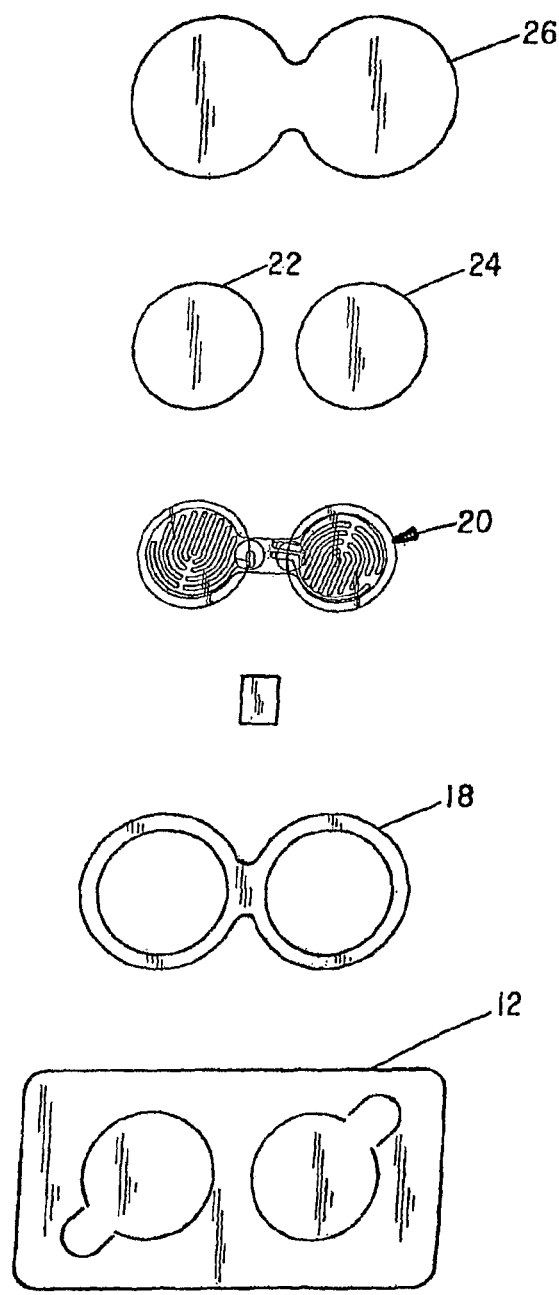
FIG. 3A is an exploded view of an integrated iontophoretic transdermal patch in accordance with one possible embodiment of the invention.
Figure 3B:
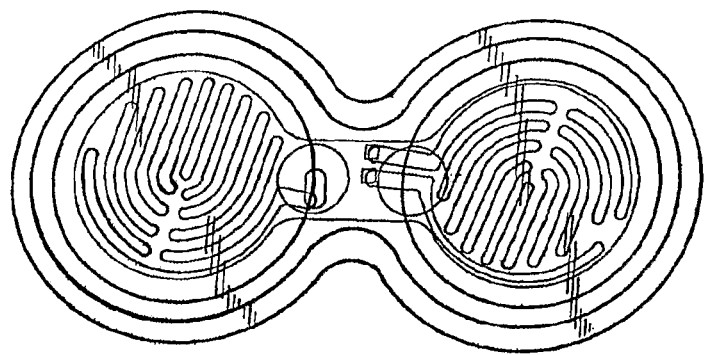
FIG. 3B is a plan view of the patch of FIG. 3A showing internal parts.
Figure 4:
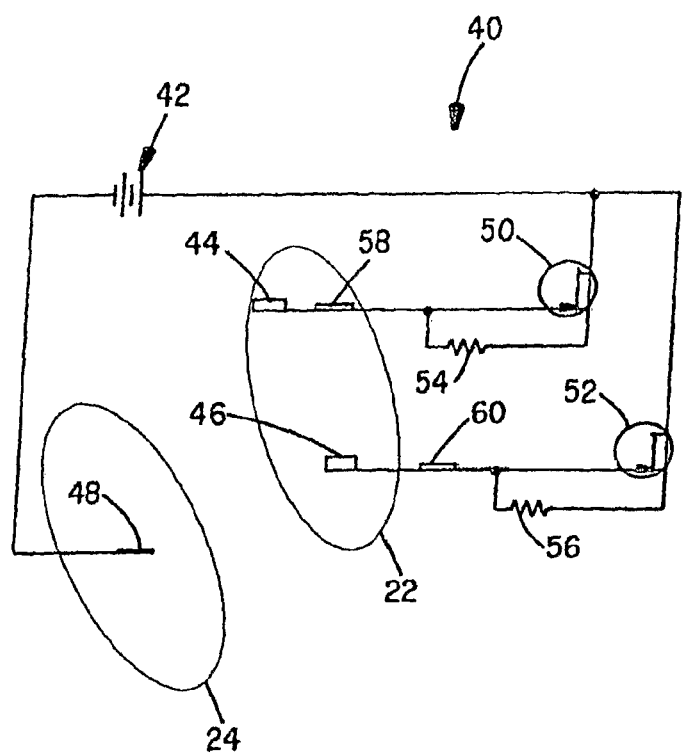
FIG. 4 is a schematic representation of a possible electrical iontophoresis circuit for use in a patch such as that shown in FIGS. 3A and 3B.

In the illustrated embodiments of FIGS. 3A, 3B and 4, activation of the patch is accomplished by application to the skin of a patient after removal of the bottom overlayer or release liner 12. This completes the circuit and activates the iontophoresis process. In the case of the circuit of FIG. 4, initially therapeutic material is supplied from both parallel connected anodes 44 and 46 to provide an initial surge or bolus of therapeutic drug. The lower capacity anode 44 depletes and is disconnected by consumption of the associated connecting wearbar 58 after a predetermined time. Thereafter, the therapeutic dose from anode 46 which may have many times the capacity of anode 44 continues to be supplied. In this manner, the wearer may be administered an initial rather high early onset dosage followed by a sustained maintenance dosage over a longer period. The times and amounts, of course, can be varied over a wide range of values and it will be appreciated that the circuit of FIG. 4 is meant to illustrate but one possible circuit. Many other configurations may occur to those skilled in the art.

A variety of electrode compositions may be used in the patches of the invention. For example, a patch should include an active electrode, or electrodes, which do not significantly react with the triptan compound or anti-migraine compound to form an insoluble salt. Zinc, or a metal with a reactivity similar to zinc is preferred. As illustrated, the electrodes, without limitation, may be zinc, zinc coated or contain zinc.

In one aspect, the invention also pertains to an iontophoretic transdermal patch for the delivery of a Sumatriptan or a salt thereof. The patch may use a two-stage patterned delivery, as in the illustrated circuit embodiment of FIG. 4. Such an embodiment may comprise a first stage which averages approximately 3 mA for about 30 minutes, followed by a second stage which averages approximately 1.5 mA for at least 1 or more hours. In one embodiment, the first stage is about 30 minutes and the second stage is about 5.5 hours.

In accordance with other embodiments, patches may be configured to employ other time-variable profiles involving multi-stage patterned deliveries of various rates and times and may include more than two stages. A multi-stage delivery that evidences a peak or crest in blood concentration levels may also be referred to as a "wave form pattern" and one such two-stage pattern is depicted in FIG. 1.

The patches of the invention are relatively light weight. An iontophoretic patch according to the invention may weigh less than about 0.5 lbs, less than about 0.4 lbs, less than about 0.3 lbs, less than about 0.2 lbs, less than about 0.1 lbs, or less than about 0.05 lbs. Alternatively, the patch may weigh less than about 500 grams, less than about 400 grams, less than about 300 grams, less than about 200 grams, less than about 100 grams, less than about 50 grams, less than about 25 grams, or even less than about 10 grams.

The therapeutic anti-migraine or triptan compound may be advantageously stored separated from electronic components of the patch. The term "separated" refers to patches where the electronic portions of the patch do not come into contact with the drug before the patch is activated.

An advantage of the iontophoretic patches of the invention using separate storage of the therapeutic compounds is that the patches have a longer "shelf life" and can be stored until the subject is suffering or is at risk of suffering from a triptan compound responsive state. In certain embodiments, the shelf life of the patch of the invention is at least 1 month or longer, at least 2 months or longer, at least 3 months or longer, at least 4 months or longer, at least 5 months or longer, at least 6 months or longer, at least 7 months or longer, at least 8 months or longer, at least 9 months or longer, at least 10 months or longer, at least 11 months or longer, at least one year or longer, at least 18 months or longer, or at least 2 years or longer.

3. Methods of Treating Subjects Using the Patches of the Invention

A. General Methods of Triptan Compound Delivery

Another aspect of the invention pertains to a method for treating a subject for a triptan compound responsive state, by administering to a subject a triptan compound according to a time-variable or steady state regimen for at least one hour, wherein the compound is administered via an iontophoretic patch.

The patches of the invention allow for the delivery of an effective amount of a triptan compound to a subject in less than about two hours, less than about 90 minutes, less than about one hour, less than about 45 minutes, less than about 30 minutes or less than about 20 minutes.

In one embodiment, the particular triptan compound is Sumatriptan and the effective amount is effective to treat a migraine. In this case, the effective amount of Sumatriptan may be a concentration of about 10 ng/mL or greater, about 11 ng/mL or greater, about 12 ng/mL or greater, about 13 ng/mL or greater, about 14 ng/mL or greater, about 15 ng/mL or greater, about 16 ng/mL or greater, about 17 ng/mL or greater, about 18 ng/mL or greater, about 19 ng/mL or greater, about 20 ng/mL or greater, about 21 ng/mL or greater, about 22 ng/mL or greater, or about 22.5 ng/mL or greater in said subject's blood or plasma. In other embodiments, the effective amount of Sumatriptan is greater than about 5 mg, greater than about 10 mg, or greater than about 15 mg.

In an embodiment, the invention pertains to an iontophoretic transdermal patch for the delivery of a triptan compound, e.g., Sumatriptan or a salt thereof, wherein the patch allows for the systemic delivery of an effective amount of Sumatriptan or a salt thereof to a subject.

In other embodiments, the patch is able to maintain a steady state concentration of the triptan compound in the subject's blood for at least one hour, for at least two hours, for at least three hours, for at least four hours, or for at least five hours or more. In yet a further embodiment, the patch allows for the delivery of an effective amount of Sumatriptan in less than about one hour.

In other embodiments, the concentration of the triptan compound in the subject's blood fluctuates from the average concentration by about 10 ng/ml or less, about 9 ng/ml or less, about 8 ng/ml or less, about 7 ng/ml or less, about 6 ng/ml or less, about 5 ng/ml or less, about 4 ng./ml or less, about 3 ng/ml or less, about 2 ng/ml or less, about 1 ng/ml or less, or by about 0.5 ng/ml or less.

B. Administration:

The invention also pertains to a method for treating a subject, by transdermally administering to the subject an effective amount of a triptan compound in less than one hour using an integrated iontophoretic patch. The patch uses a current density selected such that the current does not substantially irritate a normal subject's skin. The patch may use an average current density of 0.25 mA/cm$^2$ or less for a significant portion of the delivery time of the triptan compound.

The invention also pertains to a method for treating a triptan compound responsive state in a subject. This includes administering transdermally to the subject an effective steady state concentration of a triptan compound using an integrated patch. In one embodiment, the effective concentration is at least 20 ng/mL.

The invention also pertains to a method for treating a subject for a Sumatriptan responsive state. The method includes transdermally administering to the subject an effective amount (e.g., about 5 mg or greater, or about 10 mg or greater) of Sumatriptan or a salt thereof, such that the subject is treated. The transdermal administration may include the use of a iontophoretic patch.

In further embodiments, the triptan compound is almotriptan and the effective amount results in a $c_{max}$ of about 30-80 ng/mL, about 35-75 ng/ml, about 40-70 ng/mL, about 45-65 ng/mL, about 50-60 ng/mL or about 50-55 ng/mL. In another embodiment, the effective amount results in an AUC of about 200-400 ng.hr/mL, about 225-375 ng.hr/mL, about 250-350 ng.hr/mL, about 275-325 ng.hr/mL, or about 300-350 ng.hr/mL.

In further embodiments, the triptan compound is frovatriptan and the effective amount results in a $c_{max}$ of about 1-10 ng/mL, about 2-9 ng/mL, about 3-8 ng/mL, about 4-6 ng/mL or about 5 ng/mL. In another embodiment, the effective amount results in an AUC of about 10-80 ng.hr/mL, about 15-75 ng.hr/mL; about 20-70 ng.hr/mL; about 25-65 ng.hr/mL; about 30-60 ng.hr/mL; about 35-55 ng.hr/mL; about 40-50 ng.hr/mL or about 45 ng.hr/mL.

In yet other embodiments, the triptan compound is eletriptan and the effective amount results in a $c_{max}$ of about 50-400 ng/mL, about 75-375 ng/mL; about 100-325 ng/mL; about 125-300 ng/mL, about 150-250 ng/mL, about 175-225 ng/mL, or about 200 ng/mL. In another embodiment, the effective amount results in an AUC of about 700-1,900 ng.hr/mL; about 800-1,800 ng.hr/mL; about 900-1,700 ng.hr/mL; about 1000-1,600 ng.hr/mL; about 1100-1,500 ng.hr/mL; about 1,200-1,400 ng.hr/mL; or about 700-1,900 ng.hr/ml.

C. Methods of Triptan Compound Delivery Using a Multi-Stage or Waveform Pattern

The invention also pertains to a method for delivering therapeutic anti-migraine agents using an iontophoretic transdermal patch. In one aspect, the method of the invention includes (a) providing an iontophoretic transdermal patch containing an amount of an active anti-migraine agent in the form of a triptan compound, to be administered; (b) using an two-stage patterned delivery sequence, which may be uninterrupted and which may include an initial first stage delivery at a relatively high rate followed by a second stage delivery at a lower rate to provide a waveform delivery pattern in which a therapeutically effective dosage level is reached in a subject in generally less than one hour and a maintenance level is continued for one or more hours.

FIG. 1 is a comparative illustration of blood concentration levels measured after Sumatriptan dosing by a 50 mg oral tablet, iontophoretic dosing after application of 0.5 mA of total current for three hours, and a simulation of a preferred delivery rate pattern created from the pharmacokinetic evaluation of the 0.5 mA trial. The waveform pattern illustrates how a rapid onset of action can be created using a higher current, as well as how a sustained action can be obtained to improve the duration of action as compared to oral dosing. The rapid peak level, followed by sustained lower maintenance level, is accomplished by a simple two step current pattern, and does not require an intermediate off cycle.

In a further embodiment, the second stage comprises an average of approximately 1.5 mA for a significant portion of at least 2 hours. In another embodiment, the average current density is between about 0.05 and about 0.2 mA/cm$^2$ (e.g., about 0.1 mA/cm$^2$) during a significant portion of said first stage. In another further embodiment, the average current density is between about 0.01 and about 0.2 mA/cm$^2$ (e.g., about 0.05 mA/cm$^2$) during a significant portion of said second stage.

In a further simulation of a Sumatriptan delivery, a current level of 3 mA is used for 45 minutes (first stage), followed by a sustained current of 1.5 mA for 5 hours (second stage). This delivery pattern may be used for a transdermal patch that is superior in comparison to oral dosing.

An additional simulation of an advantageous delivery pattern for Sumatriptan shows provision of a dosage superior to nasal administration. In this configuration, a current level of 1 mA is used for 45 minutes (first stage), followed by a sustained current of 0.5 mA for 1 or more hours, 2 or more hours, 3 or more hours, 4 or more hours, or 5 hours or more (second stage). With a second stage of about 5 hours, this delivery pattern should provide a total dosage of approximately 3 mg. In a further embodiment, the average current density used in this embodiment is between about 0.05 and about 0.2 mA/cm$^2$ during a significant portion of the first stage. In a further embodiment, the average current density is between about 0.01 and about 0.2 mA/cm$^2$ during a significant portion of the second stage. In another further embodiment, the second stage averages approximately 0.5 mA for at least a significant portion of 2 hours 3 hours, 4 hours, or 5 hours.

An example of a delivery pattern for Naratriptan, which may provide a transdermal patch that may be superior in comparison to oral dosing, uses a current of 1 mA is used for a period of one hour (first stage), followed by a current of 0.25 mA for a period of at least one hour, at least two hours, at least three hours, or at least four hours (second stage) to provide a total dosage of approximately 2 mg (when the second stage lasts approximately 4 hours).

EXAMPLE I

This Example involves a study that assesses the pharmacokinetic and safety profile of an iontophoretic sumatriptan delivery system or patch in accordance with the invention in order to bridge the unmet needs in migraine treatment Using iontophoresis technology, Sumatriptan was delivered through a thin, disposable, single-use device with a self-contained galvanic power battery source and small, wafer-thin lithium battery. Each Sumatriptan patch was attached to the skin with adhesive and was designed for systemic delivery of a fixed amount of Sumatriptan, controlled by the design of the electrodes. This system was intended to provide rapid and consistent therapeutic blood levels without an injection over several hours recurrent headaches.

Delivery System (Patch)

The delivery system employed known Wearable Electronic Disposable Drug delivery technology (WEDD®) utilizes a power and control circuitry. An example of such a device is shown in FIGS. 3A, 3B and 4 described above. With WEDD, the rate that medications are delivered is regulated by applied voltage between delivery and return electrode pads and current control is regulated by integrated resistance and/or transistors incorporated into each patch. The WEDD design is simple, and amenable to creating wearable, disposable iontophoretic patches.

Several scientific studies have been completed for various patches built with WEDD technology. Delivery of dexamethasone sodium phosphate with WEDD has been described with human volunteer patients, regarding total dosage delivered and depth of penetration (C. R. Anderson, R. L. Morris, S. D. Boeh, P. C. Panus, and W. L. Sembrowich. Effects of iontophoresis current magnitude and duration on dexamethasone deposition and localized drug retention. Phys Ther. 83:161-170 (2003) and A. Chaturvedula, D. P. Joshi, C. Anderson, R. Morris, W. L. Sembrowich, and A. K. Banga. Dermal, subdermal, and systemic concentrations of granisetron by iontophoretic delivery. Pharm Res. 22:1313-1319 (2005)). WEDD technology has also been used for the delivery of fentanyl in human volunteers, where it was demonstrated that minimum effective concentrations of fentanyl were found after a 30 minute application. More recently, pharmacokinetic (PK) studies have also been reported for the delivery of granisetron and calcitonin using hairless rats with WEDD technology (A. Chaturvedula et al. (2005) and A. Chaturvedula, D. P. Joshi, C. Anderson, R. L. Morris, W. L. Sembrowich, and A. K. Banga. In vivo iontophoretic delivery and pharmacokinetics of salmon calcitonin. Int J Pharm. 297: 190-196 (2005) Based on results of in vitro studies, the amount of drug delivered by the iontophoretic patch is generally expected to be proportional to the current applied and maintain a zero-order delivery rate over time (i.e 1 mAmp should deliver about 1 mg/hour of Sumatriptan).

Methods

Patch Design

The delivery systems used in this study were prototype systems designed for the transdermal iontophoretic delivery of Sumatriptan. For this clinical study, the drug formulation was approximately 1 cc of an aqueous solution of Sumatriptan succinate (4% by weight). The solution was prepared at the clinical site, within 24 hours of the time of use. The ionized drug was delivered iontophoretically, across the stratum corneum by the second component of the system, an iontophoretic drug delivery device designed to deliver current at either 0.5 or 1.0 mA for 1.5, 3.0 or 6.0 hr as detailed below. The device used a current regulating transistor and up to four 3 volt button cell batteries attached to a Zn anode and a AgCl cathode. The drug solution is dispensed onto an absorbent pad in contact with the anode. Normal saline was placed on the absorbent pad in contact with the cathode. Current flow and drug delivery was initiated when the loaded patch, secured with a perimeter adhesive, was applied against the skin. Delivery stops when the patch is removed at the time identified in the protocol. All patches for the current study were designed to deliver a theoretical dose of 1 mg of drug per mA/hr based on previous in vitro models.

Study Design

The study was a randomized, single-center, single-dose, 4-period, pilot study of the pharmacokinetics of two prototype iontophoretic patches of Sumatriptan compared to the pharmacokinetics of 6 mg subcutaneous injection and an oral 50 mg tablet of Sumatriptan (base) as the succinate salt. Two additional periods further evaluated the patches. The subjects received all treatments at 1000 hours ±1 hour after an overnight fast. Subjects ate breakfast 3 hours pre-dosing, lunch 2.5 hours post-dosing, dinner 7.5 hours post-dosing and had snacks at 6.5 and 12 hours post-dosing. The patches were placed on a clean, relatively hair free region of the subject's upper back. For conditions in which two patches were placed simultaneously, one was placed on each side of the subject's back.

Subjects

Eight healthy adult subjects (4 males and 4 females) between 18 and 50 years of age were selected to participate in this study. The subjects received no other medication (prescription or over-the-counter) for two weeks prior to study entry. The study was conducted in six confinement periods, each lasting approximately 2 days. All subjects began confinement the morning of day −1 and remained confined until approximately 24 hours after dosing for each dosing period. There was a minimum of 3 days between each of the dosing periods.

Conditions

There were six formulations tested to allow comparison of all formulations in the same subjects. Treatment conditions included:
Treatment 1: Sumatriptan 50 mg (as the succinate salt) fast disintegrating oral tablet (Imigran Ftab® 50)
Treatment 2: Sumatriptan 6 mg (as the succinate salt) subcutaneous injection
Treatment 3: —1.0 mA patch, 10 cm2 area, 1.5 hr—theoretical dose of 1.5 mg of Sumatriptan
Treatment 4: —0.5 mA patch, 10 cm2 area, 3.0 hr—theoretical dose of 1.5 mg of Sumatriptan
Treatment 5: —two 1.0 mA patches, 10 cm2 each, 3.0 hr—theoretical dose of 6.0 mg of Sumatriptan
Treatment 6: —two 1.0 mA patches, 10 cm2 each, 6.0 hr—theoretical dose of 12.0 mg of Sumatriptan Safety Measures The following variables were included as safety endpoints: adverse events mapped to body system and preferred term using the MedDRA dictionary, skin erythema, vital signs, ECG and clinical laboratory tests including hematology and clinical chemistry. Clinical laboratory tests were drawn at screening (no more than 28 days prior to the first dosing) and on day −1 of each dosing period including HBsAg, HCV-Ab, HIV-Ab 1+2, Pregnancy Test (females only), ethanol breath test and drug screen (except HBsAg, HCV-Ab, HIV-Ab 1+2, which was done at screening only). Vital signs including blood pressure, heart rate, and temperature were also assessed pre-dosing, 30 minutes, 1, 2, 6 and 12 hours and 24 hours post dosing. Because of the possibility of local skin reaction to the patch from adhesive, current or drug, a skin erythema scale was also assessed at patch removal and at 24 hr after removal (Table I). The skin irritation assessment used a 5-point scoring system to quantify the degree of erythema present at the patch application site. This score is consistent with respect to the nominal categories used for the 5-point ordinal scale recommended by the Environmental Protection Agency (EPA) in their Health Effect Test Guidelines on acute dermal irritation. A complete physical examination was performed at screening. Vital signs were assessed at screening, at admission on day −1 and pre-dosing, 30 minutes, 1, 2, 6, 12 and 24 hours post dosing for each of the six dosing periods. Additionally, an electrocardiogram was performed at screening and day 2 for each of periods 4 and 6. Vital signs were assessed at screening, at admission on day −1 and pre-dosing, 30 minutes, 1, 2, 6, 12 and 24 hours post-dosing for each of the four dosing periods.

Pharmacokinetic Measures

Blood samples were collected after drug administration to determine plasma Sumatriptan concentrations. Plasma samples were analyzed using a validated HPLC-MS/MS method (PPD, Middleton, Va.). The pharmacokinetic profile of each formulation was assessed including calculation of area under the drug concentration-time curve from time zero to 24 hours. (AUC 0-24), area under the drug concentration-time curve up to the last measurable concentration extrapolated to infinity (AUC∞), time of maximum drug concentration (Tmax), maximum observed drug concentration (Cmax), total body clearance (Cl) and terminal elimination half-life (T½), using model-independent methods with nonlinear least-square regression analysis. Clearance obtained from the 6 mg sc injection was used to calculate the dose delivered during iontophoretic delivery based on the assumption that iontophoretic delivery provides a zero order delivery rate. The dose delivered during iontophoretic application was calculated using the equation: F*Dose delivered=AUC 0-∞ iontophoretic* Clearance sc with F equal to the fraction of dose absorbed into systemic circulation. Additionally, clinical chemistry and hematology profiles were obtained at screening and prior to each dosing period. Sixteen blood samples were collected at 0, 15, 30 minutes and 1, 1.5, 2, 3, 4, 5, 6, 7, 8, 10, 12, 16 and 24 hours post-dosing for each of the four dosing periods. Four formulations of Sumatriptan patch were tested. The reference therapies included 6 mg of Sumatriptan subcutaneous injection and 50 mg of oral Sumatriptan delivered as a single 50 mg tablet. Doses are expressed as Sumatriptan free base for subcutaneous and oral formulations.

Results

Subjects

A total of 8 subjects received study medication and 8 subjects completed the study as per protocol. All study subjects were of Caucasian race with the mean age being 32.3 years.

Pharmacokinetics

Four preparations of the sumatriptan patch were compared to injectable and oral preparations. All pharmacokinetic parameters including AUC(0-inf) (ng.hr/mL), AUC(0-24) (ng.hr/mL), CL (L/hr), Cmax (ng/mL), Tmax (hr), T½ (hr) for each preparation are listed in Table III. First, 50 mg oral formulations (Treatment 1) and the 6 mg Sumatriptan injection (Treatment 2) was compared with the patch delivering 0.5 mA for 3 hours (Treatment 3) or 1 mA for 1.5 hours (Treatment 4). The amount of drug delivered for the 1 mA patch for 1.5 hours and the 0.5 mA patch for 3 hours was 1.45 mg, compared to a theoretical dose of 1.5 mg. These data showed that the mean AUC0-24 and Cmax for both patch conditions were significantly lower than either oral or injection. The AUC for both the patches in this part of the example were approximately 20% of the oral and 27% of the injection. Cmax was 30% of oral and 14% of injection for Treatment 3 and 20% of oral and 5% of injection for Treatment 4 (Table II). Following the favorable safety profile and minimal skin irritation from patch Treatments 3 and 4, two additional treatments were initiated. Treatment 5 delivered a total of 2 mA for 3 hours from a pair of 1 mA patches and Treatment 6 delivered 2 mA for 6 hours from a pair of 1 mA patches. Treatment 5 (3 hour 2 mA patches) yielded an AUC value which was approximately 86% of the 50 mg oral preparation and 122% of the 6 mg injection. Treatment 6 (6 hour, 2 mA patches) yielded an AUC that was approximately 182% of the 50 mg oral preparation and 257% of the 6 mg injection. Cmax was 108% of oral and 48% of injection for Treatment 5 and 131% of oral and 59% of the injection for Treatment 6.

Trends

AUC for the patches increased proportionally as a function of current-time intervals and Cmax were proportional to current. Apparent Tmax for the patches ranged from 1.5 to 4.1 hour in proportion to the length of time the patch was administered. Because of the sustained plateau for Sumatriptan level with the patches, the Tmax was not a peak as noted for both oral and injectable preparations. Rather, maximum serum concentration was reached in approximately 1.5 hour for all patch formulations and is maintained at that level until patch removal. The 3 hour and 6 hour 2 mA patches maintained Sumatriptan levels above 10 ng/mL for 4 and 7 hours respectively, as compared to approximately 3 hours for oral and 1.5 hours for injectable (FIG. 1). Thus, the patch of the invention was capable of maintaining proposed therapeutic Sumatriptan levels for four times longer than the 6.0 mg injection and twice as long as the 50 mg oral preparation, offering substantially longer duration of treatment than either preparation. The elimination half life for the subcutaneous formulation was approximately 2 hours. The elimination half-life after removing the patch was also 2 hours and was similar across all different treatments.

Safety

The patches of the invention were generally well tolerated with fewer adverse events than the 6 mg subcutaneous injection. Adverse events that were more prevalent for the patches than other formulations were noted only as minor localized sensations and reactions at the patch site. Of course, pad skin contact area can be varied to adjust current density and reduce the possibility of shin irritation as needed.

Skin Erythema

Skin erythema scores are noted in Table IV. For Treatment 6, one subject requested the 6.0 hour two 1 mA patches be removed 34 minutes prior to the scheduled time due to discomfort at the patch site. For Treatment 6, the drug and saline solutions appeared to leak in three subjects. Solution leakage from the patches may have resulted in uneven current density in the patch with areas of increased current density which resulted in some irritation. The investigator concluded that leaking of fluid was likely to have affected the score of erythema for subject three.

Vital Signs, Clinical Laboratories and ECG

In this Example, no abnormal findings were reported as an adverse event from the physical examination, electrocardiogram, clinical laboratories, or vital sign measurements.

Discussion

The Example demonstrates pharmacokinetic data and safety profile for an iontophoretic patch delivery system for the anti-migraine medication Sumatriptan in accordance with the invention. This system has the potential to fill an unmet need in migraine care by providing a less invasive systemic delivery of the most widely prescribed and preferred tripatan. Because this is a transdermal formulation, it circumvents concerns about taking an oral medication during an attack that may have nausea and vomiting, often associated with gastroparesis, among the prominent or presenting symptoms.

Additionally, the iontophoretic patch system can deliver steady state, therapeutic drug levels for significantly longer periods of time than are achievable from subcutaneous injections or nasal preparations. This is particularly important in helping patients avoid recurrence that is likely due to the rapid metabolism of bolus injections that result from the short half life of Sumatriptan.

Improved drug delivery systems represent a logical, cost effective and expedient alternative to trying to develop an equally efficacious medication with longer half-life.(M. Hans, L. Dan, K. Winey, A. Lowman, and S. J. Siegel. Daily to Annual Biodegradable Drug Delivery Strategies for Psychoactive Compounds:. In S. K. Mallapragada (ed.), Handbook of Biodegradable Polymeric Materials & Applications, American Scientific Publishers, Stevenson Ranch, Calif., 2004) and S. Siegel. Extended Release Drug Delivery Strategies in Psychiatry: Theory to Practice. Psychiatry 2005. 2:22-31 (2005)) It also obviates the need for painful injections with the subcutaneous preparation or the severely unpleasant taste that is commonly reported from nasal preparations. Additional advantages for patches include lower Cmax with comparable AUC, yielding a safer delivery profile with less severe and fewer side effects. The latter was evident in the current study with less adverse events among the patch conditions than the injectable formulation.

Patches demonstrated a linear relationship between current and Sumatriptan delivery as predicted, validating previous in vitro models during development. (C. R. Anderson et al. (2003); G. A. Lattin, R. V. Padmanabhan, and J. B. Phipps. Electronic control of iontophoretic drug delivery. Ann N Y Acad Sci. 618:450-464 (1991); and C. Anderson, S. Boeh, R. Morris, W. Sembrowich, and P. Panus. Quantification of Total Dexamethasone Phosphate Delivery by Iontophoresis. International Journal of Pharmaceutical Compounding. 7: (2003)) Initial trials with 1.5 mA-hr patches (1 mA for 1.5 hr or 0.5 mA for 3 hr) yielded very good tolerability. Based on the high tolerability with initial patch design, subsequent patches were tested at higher current-time intervals. Patches delivering 6 and 12 mA hr yielded more favorable Sumatriptan systemic profiles, with the 2 mA-6 hr design delivering drug at a rate that maintained the target level of 10 ng/mL for greater than 7 hr, supporting the hypothesis that the iontophoretic Sumatriptan patch may be able to maintain therapeutically appropriate steady state drug levels for longer intervals than currently possible with either 50 mg oral or 6 mg injectable formulations.

It should be noted that the oral formulation in the current study yielded a longer terminal elimination half-life than anticipated. The apparent T½ for the oral formulation was 5.9 hr, possibly because subjects were allowed to eat prior to and following administration. Additionally, the terminal half-life may have appeared greater than previously reported because of the high sensitivity of the LCMS method used (limit of quantification=0.20 ng/mL), resulting in quantification of clinically insignificant levels and possibly reflecting the presence of a deep compartment.(C. Duquesnoy, J. Mamet, D. Sumner, and E. Fuseau. Comparative clinical pharmacokinetics of single doses of Sumatriptan following subcutaneous, oral, rectal and intranasal administration. Eur J Pharm Sci. 6:99-104 (1998) and S. Jhee, T. Shiovitz, A. Crawford, and N. Cutler. Pharmacokinetics and pharmacodynamics of the triptan antimigraine agents: a comparative review. Clin Pharmacokinet. 40:189-205 (2001)

TABLE II

Erythema scale utilized to rate the degree of skin irritation from patches.

| Score | Definition |
|---|---|
| 0 | No erythema |
| 1 | Minimal erythema |
| 2 | Moderate erythema with sharply defined borders |
| 3 | Intense erythema with or without oedema |
| 4 | Intense erythema with oedema and blistering/erosion |

TABLE III

Pharmacokinetic results for patches as compared with oral and injectable formulations are presented. Sumatriptan Pharmacokinetic Data Arithmetic Means (CV%)

| | Comparators | | NP101 Patches | | | |
|---|---|---|---|---|---|---|
| Treatment | 1 | 2 | 3 | 4 | 5 | 6 |
| Theoretical dose | | | 1.5 mg | 1.5 mg | 6.0 mg | 12.0 mg |
| Dose delivered | 50.0 mg | 6.0 mg | 1.45 mg | 1.45 mg | 7.4 mg | 15.7 mg |
| PK Parameter | P.O. (n = 8) | sub-q (n = 8) | 1.5 hr 1 mA (n = 8) | 3.0 hr 0.5 mA (n = 8) | 3.0 hr 2 mA (n = 8) | 6.0 hr 2 mA (n = 7) * |
| $AUC_{(0-inf)}$ (ng · hr/mL) | 103.50 (34.06) | 73.45 (14.77) | 19.68 (25.28) | 19.58 (51.27) | 89.15 (53.93) | 188.60 (27.51) |
| $AUC_{(0-24)}$ (ng · hr/mL) | 100.99 (34.54) | 72.96 (15.00) | 19.16 (25.71) | 19.00 (53.33) | 88.87 (54.22) | 189.11 (27.50) |
| CL (L/hr) | 532.03 (32.50) | 83.07 (13.05) | 78.03 (25.80) | 93.58 (56.49) | 123.89 (94.83) | 89.51 (30.72) |
| $C_{max}$ (ng/mL) | 26.41 (26.71) | 58.42 (24.48) | 8.29 (27.09) | 5.21 (49.10) | 28.66 (65.86) | 34.63 (34.68) |

TABLE III-continued

Pharmacokinetic results for patches as
compared with oral and injectable formulations are
presented. Sumatriptan Pharmacokinetic Data Arithmetic Means (CV%)

|  | Comparators | | NP101 Patches | | | |
| --- | --- | --- | --- | --- | --- | --- |
| Treatment | 1 | 2 | 3 | 4 | 5 | 6 |
| $T_{max}$ (hr) | 1.31 | 0.28 | 1.50 | 2.30 | 2.22 | 4.14 |
|  | (83.80) | (31.43) | (0.00) | (30.29) | (34.83) | (45.00) |
| $T_{1/2}$ (hr) | 5.93 | 2.02 | 1.88 | 2.05 | 2.05 | 2.11 |
|  | (33.31) | (11.04) | (14.53) | (24.88) | (13.67) | (7.01) |

*-Subject 8 was excluded from pK analyses in Treatment 6 due to early removal of her patch.

TABLE IV

| Subject # | Treatment 3 1.5 hr 1 mA Patch | | Treatment 4 3.0 hr 0.5 mA Patch | | Treatment 5 3.0 hr 2 mA Patches | | | | Treatment 6 6.0 hr 2 mA Patches | | | |
| --- | --- | --- | --- | --- | --- | --- | --- | --- | --- | --- | --- | --- |
|  | Removal | 24 Hr | Removal | 24 Hr | Removal | | 24 hr | | Removal | | 24 hr | |
|  |  |  |  |  | Left | Right | Left | Right | Left | Right | Left | Right |
| 1 | 1 | 1 | 1 | 0 | 1 | 1 | 1z | 0 | 2 | 2 | 2 | 2 |
| 2 | 1 | 0 | 1 | 0 | 1 | 1 | 1 | 1 | 2 | 2 | 1 | 1 |
| 3 | 1 | 1 | 1 | 0 | 1 | 1 | 1 | 1 | 1 | 2 | 1 | 4 |
| 4 | 1 | 1 | 1 | 1 | 1 | 1 | 1 | 1 | 2 | 2 | 1 | 1 |
| 5 | 1 | 0 | 1 | 1 | 1 | 1 | 1 | 0 | 1 | 1 | 1 | 1 |
| 6 | 1 | 1 | 1 | 1 | 1 | 1 | 1 | 1 | 1 | 1 | 1 | 1 |
| 7 | 1 | 1 | 1 | 1 | 1 | 2 | 1 | 1 | 1 | 1 | 2 | 1 |
| 8 | 2 | 1 | 1 | 0 | 1 | 1 | 1 | 1 | 2 | 1 | 1 | 1 |

Erythema scores for all periods, n = 8 for all conditions.
Treatment 3 and 4 had a single patch application.
Treatments 5 and 6 utilized 2 patches each to create a larger surface area with reduced current density as planned for future design modifications based on the results of these studies.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. An integrated iontophoretic transdermal patch for the delivery of a triptan compound or a salt thereof to a human subject, the patch comprising:
   the triptan compound or the salt thereof disposed in a drug reservoir;
   a return reservoir; and
   an electronic circuit in electrical connection with the reservoirs, the electronic circuit comprising:
      a voltage source;
      an active electrode;
      a return electrode; and
      a transistor,
   wherein the electronic circuit is pre-configured to provide a two-stage delivery sequence including:
      a first bolus stage delivery in which an average current density on the skin of the subject through the drug reservoir and an average current density on the skin of the subject through the return reservoir are each between about 0.05 and about 0.20 mA/cm² during at least 30% of the delivery time of the first bolus stage delivery and during which the current through the skin of the subject and the drug reservoir is sufficient to achieve a therapeutically effective dosage level of at least 10 ng/mL of the triptan compound or the salt thereof in the plasma of the human subject in less than one hour; and
      a second maintenance stage delivery in which an average current density on the skin of the subject through the drug reservoir and an average current density on the skin of the subject through the return reservoir are each between about 0.01 and about 0.2 mA/cm² during at least 30% of the delivery time of said second maintenance stage delivery and are each lower than both the average current density on the skin of the subject through the drug reservoir and the average current density on the skin of the subject through the return reservoir during the first bolus stage delivery.

2. The patch of claim 1, wherein the active electrode comprises zinc or zinc coating.

3. The patch of claim 1, wherein the triptan compound or the salt thereof is formulated in a flowable hydrogel.

4. The patch of claim 1, wherein the electronic circuit further comprises a pair of control transistors in electrical connection with two or more resistors.

5. The patch of claim 1, wherein the voltage source is a galvanic power battery source.

6. The patch of claim 1, wherein the voltage source is a lithium battery.

7. The patch of claim 1, wherein the triptan compound or the salt thereof is selected from sumatriptan, naratriptan and salts thereof.

8. The patch of claim 1, wherein the triptan compound or the salt thereof is sumatriptan or a salt thereof.

9. The patch of claim 1, wherein the triptan compound or the salt thereof is sumatriptan succinate.

10. The patch of claim 1, wherein the triptan compound or the salt thereof is separated from the electronic circuit prior to patch activation.

11. The patch of claim 1, wherein the electronic circuit is operative to maintain a steady state concentration of the triptan compound in the subject's plasma for at least one hour.

12. The patch of claim 11, wherein the steady state concentration is a plasma concentration of about 10 ng/mL or greater.

13. The patch of claim 11, wherein the electronic circuit is operative to maintain the steady state concentration of the triptan compound for at least four hours.

14. The patch of claim 1, wherein said patch has a shelf life of at least 6 months.

15. The patch of claim 1, wherein said patch weighs less than about 0.1 lb.

\* \* \* \* \*